United States Patent
Zhang et al.

(10) Patent No.: US 12,351,535 B2
(45) Date of Patent: Jul. 8, 2025

(54) COKE CONTROL REACTOR, DEVICE FOR PREPARING LOW-CARBON OLEFINS FROM OXYGEN-CONTAINING COMPOUND, AND USE THEREOF

(71) Applicant: DALIAN INSTITUTE OF CHEMICAL PHYSICS, CHINESE ACADEMY OF SCIENCES, Dalian (CN)

(72) Inventors: Tao Zhang, Dalian (CN); Mao Ye, Dalian (CN); Jinling Zhang, Dalian (CN); Shuliang Xu, Dalian (CN); Hailong Tang, Dalian (CN); Xiangao Wang, Dalian (CN); Cheng Zhang, Dalian (CN); Jinming Jia, Dalian (CN); Jing Wang, Dalian (CN); Hua Li, Dalian (CN); Chenggong Li, Dalian (CN); Zhongmin Liu, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 198 days.

(21) Appl. No.: 17/801,811

(22) PCT Filed: Oct. 16, 2020

(86) PCT No.: PCT/CN2020/121567
§ 371 (c)(1),
(2) Date: Aug. 24, 2022

(87) PCT Pub. No.: WO2022/077458
PCT Pub. Date: Apr. 21, 2022

(65) Prior Publication Data
US 2023/0085715 A1 Mar. 23, 2023

(51) Int. Cl.
*C07C 1/20* (2006.01)
*B01J 8/18* (2006.01)
(Continued)

(52) U.S. Cl.
CPC ............... *C07C 1/20* (2013.01); *B01J 8/1809* (2013.01); *B01J 8/228* (2013.01); *B01J 8/26* (2013.01); *C07C 2529/85* (2013.01)

(58) Field of Classification Search
CPC ...... B01J 8/24; B01J 8/26; C07C 1/20; C07C 11/06; C07C 11/16
See application file for complete search history.

(56) References Cited

U.S. PATENT DOCUMENTS

| 4,304,659 A | 12/1981 | Pratt et al. |
| 5,714,662 A | 2/1998 | Vora et al. |
| 8,894,940 B2 * | 11/2014 | Krishnamurthy ...... B01J 8/1827 422/220 |

FOREIGN PATENT DOCUMENTS

| CN | 101696145 A | 4/2010 |
| CN | 102086402 A | 6/2011 |

(Continued)

OTHER PUBLICATIONS

Basic building blocks of a fluidised bed reactor, Solid Fluidisation and Applications, Department of Personnel and Education, Ministry of Chemical Industry; Education and Training Centre of the Ministry of Chemical Industry; Chemical Industry Press, 1997, pp. 95-96.

(Continued)

*Primary Examiner* — Sharon Pregler
(74) *Attorney, Agent, or Firm* — Bayramoglu Law Offices LLC (57) ABSTRACT

A coke control reactor, a device for preparing low-carbon olefins from an oxygen-containing compound, and a use (Continued)

thereof are provided. The coke control reactor includes a riser reactor and a bed reactor; the bed reactor includes a bed reactor shell, and the bed reactor shell encloses a reaction zone I, a transition zone, and a gas-solid separation zone I from bottom to top; a bed reactor distributor is arranged in the reaction zone I; a coke controlled catalyst delivery pipe is arranged outside the reaction zone I; an upper section of the riser reactor penetrates through a bottom of the bed reactor and is axially inserted in the bed reactor; and an outlet end of the riser reactor is located in the transition zone. The coke control reactor can control the conversion and generation of coke species in a catalyst.

3 Claims, 1 Drawing Sheet

(51) Int. Cl.
  *B01J 8/22* (2006.01)
  *B01J 8/26* (2006.01)

(56) References Cited

FOREIGN PATENT DOCUMENTS

| | | | |
|---|---|---|---|
| CN | 102190548 A | 9/2011 | |
| CN | 102276406 A | 12/2011 | |
| CN | 102295508 A | 12/2011 | |
| CN | 102875282 A | 1/2013 | |
| CN | 102875296 A | 1/2013 | |
| CN | 107961743 A | * 4/2018 | ............ B01J 8/0055 |
| CN | 110818522 A | 2/2020 | |
| CN | 111004077 A | 4/2020 | |
| CN | 111099945 A | 5/2020 | |
| KR | 20110081178 A | 7/2011 | |
| KR | 20150038043 A | 4/2015 | |
| KR | 20160086907 A | 7/2016 | |
| KR | 20160093676 A | 8/2016 | |
| RU | 2460581 C2 | 9/2012 | |
| WO | 2015081489 A1 | 6/2015 | |

OTHER PUBLICATIONS

Chunliang Yuan, Influence of carbon deposits on the operating process of methanol-to-olefin industrial plants, M-Sized Nitrogenous Fertilizer Progress, 2019, pp. 41-45, No. 3.

Weiguo Song, et al., Selective Synthesis of Methylnaphthalenes in HSAPO-34 Cages and Their Function as Reaction Centers in Methanol-to-Olefin Catalysis, J. Phys. Chem. B, 2001, pp. 12839-12843, vol. 105.

Liu Shenghai, et al., Study on and application of pre-carbon deposition technology of methanol to olefin catalyst Petrochemical Technology, 2020, pp. 910-913, vol. 49 N0.9.

* cited by examiner

COKE CONTROL REACTOR, DEVICE FOR PREPARING LOW-CARBON OLEFINS FROM OXYGEN-CONTAINING COMPOUND, AND USE THEREOF

CROSS REFERENCE TO THE RELATED APPLICATIONS

This application is the national phase entry of International Application No. PCT/CN2020/121567, filed on Oct. 16, 2020, the entire contents of which are incorporated herein by reference.

TECHNICAL FIELD

The present application relates to a coke control reactor, a device for preparing low-carbon olefins from an oxygen-containing compound, and use thereof, and belongs to the field of chemical catalytic devices.

BACKGROUND

Methanol-to-olefin technology (MTO) mainly includes DMTO (methanol-to-olefin) technology of Dalian Institute of Chemical Physics, Chinese Academy of Sciences and MTO technology of UOP Company of the United States. In 2010, the Shenhua Baotou methanol-to-olefin plant using DMTO technology was completed and put into operation. This is the world's first industrial application of MTO technology. As of the end of 2019, 14 DMTO industrial plants have been put into production, with a total production capacity of about 8 million tons of low-carbon olefins per year.

In recent years, DMTO technology has been further developed, and a new generation of DMTO catalyst with better performance have gradually begun industrial applications, creating higher benefits for DMTO plants. The new generation of DMTO catalyst has higher methanol processing capacity and low-carbon olefin selectivity. It is difficult for the existing DMTO industrial devices to take full advantage of the advantages of the new generation of DMTO catalyst. Therefore, it is necessary to develop a DMTO device and production method that can meet the needs of a new generation of DMTO catalyst with high methanol processing capacity and high selectivity of low-carbon olefins.

SUMMARY

According to a first aspect of the present application, a coke control reactor is provided, which can control the conversion and generation of coke species in a catalyst. On the one hand, inactive large-molecule coke species remaining in a regenerated catalyst are converted into small-molecule coke species; and on the other hand, a riser reactor raw material and a bed reactor raw material can also enter the catalyst to generate highly-active small-molecule coke species, and the small-molecule coke species are mainly polymethylbenzene and polymethylnaphthalene, which can improve the selectivity for ethylene.

The coke control reactor includes a riser reactor and a bed reactor; the bed reactor includes a bed reactor shell, and the bed reactor shell encloses a reaction zone I, a transition zone, and a gas-solid separation zone I from bottom to top; a bed reactor distributor is arranged in an inner lower part of the reaction zone I; a coke controlled catalyst delivery pipe is arranged outside the reaction zone I; an upper section of the riser reactor penetrates through a bottom of the bed reactor and is axially inserted in the bed reactor; and an outlet end of the riser reactor is located in the transition zone.

Specifically, the coke controlled catalyst delivery pipe is configured to deliver a coke controlled catalyst to the next-level reactor, such as a methanol conversion reactor.

Optionally, at least one perforated plate may be arranged in the reaction zone I; and if there are a plurality of perforated plates, the plurality of perforated plates may be axially arranged on a periphery of the riser reactor in sequence; the outlet end of the riser reactor may be located above the perforated plate; and the bed reactor distributor may be located below the perforated plate.

Specifically, the perforated plate may be arranged horizontally, and a periphery of the perforated plate may abut against an inner wall of the bed reactor, such that a stream can pass through apertures in the perforated plate.

Optionally, the perforated plate may have a porosity of 1% to 30%.

Optionally, the gas-solid separation zone I may be provided with a bed reactor gas-solid separator and a bed reactor gas collection chamber; a gas outlet of the bed reactor gas-solid separator may communicate with the bed reactor gas collection chamber; a catalyst outlet of the bed reactor gas-solid separator may be formed above the perforated plate; and the bed reactor gas collection chamber may communicate with a coke control product gas delivery pipe located outside the bed reactor.

Specifically, the bed reactor gas-solid separator may be a bed reactor gas-solid cyclone separator.

Specifically, an inner top of the bed reactor may be provided with a bed reactor gas collection chamber; and a catalyst outlet of the bed reactor gas-solid cyclone separator may be located below the outlet end of the riser reactor.

Optionally, the bed reactor distributor may be configured to feed a bed reactor raw material; and the bed reactor raw material may include 0 wt % to 20 wt % of hydrogen, 0 wt % to 50 wt % of methane, 0 wt % to 50 wt % of ethane, 0 wt % to 20 wt % of ethylene, 0 wt % to 50 wt % of propane, 0 wt % to 20 wt % of propylene, 0 wt % to 90 wt % of butane, 0 wt % to 90 wt % of butene, 0 wt % to 90 wt % of pentane, 0 wt % to 90 wt % of pentene, 0 wt % to 90 wt % of hexane, 0 wt % to 90 wt % of hexene, 0 wt % to 50 wt % of methanol, 0 wt % to 50 wt % of ethanol, and 0 wt % to 50 wt % of water, and a total content of methanol, ethanol, and water may be greater than or equal to 10 wt %.

Optionally, the riser reactor may be configured to feed a catalyst and a riser reactor raw material; and the riser reactor raw material may include 0 wt % to 20 wt % of hydrogen, 0 wt % to 50 wt % of methane, 0 wt % to 50 wt % of ethane, 0 wt % to 20 wt % of ethylene, 0 wt % to 50 wt % of propane, 0 wt % to 20 wt % of propylene, 0 wt % to 90 wt % of butane, 0 wt % to 90 wt % of butene, 0 wt % to 90 wt % of pentane, 0 wt % to 90 wt % of pentene, 0 wt % to 90 wt % of hexane, 0 wt % to 90 wt % of hexene, 0 wt % to 50 wt % of methanol, 0 wt % to 50 wt % of ethanol, and 0 wt % to 50 wt % of water, and a total content of methanol, ethanol, and water may be greater than or equal to 10 wt %.

According to a second aspect of the present application, a device for preparing low-carbon olefins from an oxygen-containing compound is also provided, including a methanol conversion reactor and the coke control reactor described above.

The low-carbon olefins mentioned in the present application refer to ethylene and propylene.

Optionally, the methanol conversion reactor may include a methanol conversion reactor shell and a delivery pipe; the methanol conversion reactor shell may include a lower shell and an upper shell; the lower shell may enclose a reaction zone II, and a methanol conversion reactor distributor may be arranged in an inner lower part of the reaction zone II; the delivery pipe may be axially located above the reaction zone II; the delivery pipe may have one end closed and the other end communicating with the reaction zone II; the upper shell may be arranged on a periphery of the delivery pipe; the upper shell and a pipe wall of the delivery pipe may enclose to a cavity; the cavity may be divided into a spent catalyst zone and a gas-solid separation zone II from bottom to top; and the spent catalyst zone may be provided with a spent catalyst zone gas distributor.

Specifically, the upper shell may be arranged on a periphery of the delivery pipe in a wrapping form. The methanol conversion reactor distributor may be configured to feed a raw material with an oxygen-containing compound; and the spent catalyst zone gas distributor may be configured to feed a spent catalyst zone fluidizing gas.

Optionally, the gas-solid separation zone II may be provided with a first gas-solid separation unit of the methanol conversion reactor; an upper part of the delivery pipe may be connected to an inlet of the first gas-solid separation unit of the methanol conversion reactor; a catalyst outlet of the first gas-solid separation unit of the methanol conversion reactor may be formed in the spent catalyst zone; a gas outlet of the first gas-solid separation unit of the methanol conversion reactor may communicate with a methanol conversion reactor gas collection chamber; and the methanol conversion reactor gas collection chamber may be connected to a product gas delivery pipe.

Optionally, the gas-solid separation zone II may be further provided with a second gas-solid separation unit of the methanol conversion reactor; a gas inlet of the second gas-solid separation unit of the methanol conversion reactor may be formed in the gas-solid separation zone II; a catalyst outlet of the second gas-solid separation unit of the methanol conversion reactor may be formed in the spent catalyst zone; and a gas outlet of the second gas-solid separation unit of the methanol conversion reactor may communicate with the methanol conversion reactor gas collection chamber.

Optionally, the spent catalyst zone gas distributor may be located below the first gas-solid separation unit of the methanol conversion reactor and the second gas-solid separation unit of the methanol conversion reactor; and a methanol conversion reactor cooler may be further provided in the spent catalyst zone.

Optionally, a spent catalyst circulation pipe and a spent catalyst inclined pipe may be further arranged outside the spent catalyst zone; the spent catalyst circulation pipe may be configured to connect the spent catalyst zone and the reaction zone II; and the spent catalyst inclined pipe may be configured to output a spent catalyst.

Specifically, the spent catalyst circulation pipe may be configured to deliver a part of the spent catalyst in the spent catalyst zone to the reaction zone II. The spent catalyst circulation pipe may be provided with a spent catalyst circulation slide valve.

Optionally, the gas-solid separation zone II may communicate with the bed reactor gas collection chamber through a coke control product gas delivery pipe; and the reaction zone II may communicate with the reaction zone I through a coke controlled catalyst delivery pipe.

Specifically, a coke controlled catalyst slide valve may be further provided on the coke controlled catalyst delivery pipe.

Optionally, the device may further include a regenerator; the regenerator may be connected to the spent catalyst inclined pipe, such that a spent catalyst is able to be delivered to the regenerator; the regenerator may be connected to a riser reactor, such that a regenerated catalyst may be able to be delivered to the coke control reactor; and an inner bottom of the regenerator may be provided with a regenerator distributor.

Specifically, the regenerator distributor may be configured to feed a regeneration gas.

Optionally, a bottom of the regenerator may be further provided with a regenerator stripper; an upper section of the regenerator stripper may be arranged inside the regenerator, and an inlet of the upper section of the regenerator stripper may be located above the regenerator distributor; a lower section of the regenerator stripper may be arranged outside the regenerator, and an outlet of the lower section of the regenerator stripper may be connected to the riser reactor; and the regenerator stripper may be further provided with a regenerator cooler.

Optionally, the regenerator may be connected to the spent catalyst inclined pipe through a spent catalyst delivery pipe and a methanol conversion reactor stripper; and the regenerator may be connected to an inlet of the riser reactor through the regenerator stripper and a regenerated catalyst inclined pipe.

Specifically, a spent catalyst slide valve may be arranged between the spent catalyst delivery pipe and the methanol conversion reactor stripper; and an inlet of the spent catalyst slide valve may be connected to a bottom of the methanol conversion reactor stripper through a pipeline, and an outlet of the spent catalyst slide valve may be connected to an inlet of the spent catalyst delivery pipe through a pipeline.

A regenerated catalyst slide valve may be arranged between the regenerator stripper and the regenerated catalyst inclined pipe; and an inlet of the regenerated catalyst slide valve is connected to a bottom of the regenerator stripper through a pipeline, and an outlet of the regenerated catalyst slide valve is connected to an inlet of the regenerated catalyst inclined pipe through a pipeline.

Optionally, the regenerator may be further provided with a regenerator gas-solid separation unit and a regenerator gas collection chamber; a catalyst outlet of the regenerator gas-solid separation unit may be formed above the regenerator distributor; a gas outlet of the regenerator gas-solid separation unit may be connected to the regenerator gas collection chamber; and the regenerator gas collection chamber may be connected to a flue gas delivery pipe located outside the regenerator.

According to a third aspect of the present application, a method for on-line modification of a DMTO catalyst is also provided, including feeding a riser reactor raw material and a catalyst into a transition zone from a riser reactor, and feeding a bed reactor raw material into a reaction zone I; and allowing the catalyst to contact and react with the riser reactor raw material and the bed reactor raw material to generate a coke controlled catalyst and a coke control product gas, where the catalyst is a DMTO catalyst; and the coke controlled catalyst is a modified DMTO catalyst.

Optionally, an active component of the catalyst may be an SAPO-34 molecular sieve.

In the present application, the catalyst entering the riser reactor may be a fresh catalyst or a regenerated catalyst and preferably a regenerated catalyst, such that both coke control and catalyst regeneration can be realized on-line.

Optionally, the catalyst may be a regenerated catalyst; and a coke content in the regenerated catalyst may be less than or equal to 3 wt %.

Optionally, a coke content in the coke controlled catalyst may be 4 wt % to 9 wt %.

Optionally, a quartile deviation of a coke content distribution in the coke controlled catalyst may be less than 1 wt %. Specifically, in the present application, the coke content in the coke controlled catalyst is controlled at 4 wt % to 9 wt % through the arrangement of the coke control reactor and the selection of the coke control process. Since the catalyst is granular, the coke content in the catalyst refers to an average coke content in catalyst granules, but coke contents in different catalyst granules may actually be different. In the present application, the quartile deviation of the coke content distribution in the coke controlled catalyst can be controlled to be less than 1 wt %, such that the overall coke content distribution of the catalyst is narrow, thereby improving the activity of the catalyst and the selectivity for low-carbon olefins.

Optionally, coke species in the coke controlled catalyst may include polymethylbenzene and polymethylnaphthalene; a total mass of the polymethylbenzene and the polymethylnaphthalene may account for greater than or equal to 70 wt % of a total mass of coke; a mass of coke species with a molecular weight greater than 184 may account for less than or equal to 25 wt % of the total mass of coke; and the total mass of coke may refer to a total mass of coke species.

In the present application, types and contents of coke species are also very important, which is also one of the objectives of control in the present application. In the present application, a total mass of the polymethylbenzene and the polymethylnaphthalene is controlled to be greater than or equal to 70 wt % of the total mass of coke through the arrangement of coke control and the selection of coke control process parameters to improve the activity of the catalyst and the selectivity for low-carbon olefins.

Optionally, process operating conditions of the riser reactor may be as follows: apparent gas linear velocity: 3 m/s to 10 m/s; reaction temperature: 400° C. to 700° C.; reaction pressure: 100 kPa to 500 kPa; and bed density: 10 kg/m$^3$ to 150 kg/m$^3$.

Optionally, process operating conditions of the reaction zone I of a bed reactor may be as follows: apparent gas linear velocity: 0.1 m/s to 1.0 m/s; reaction temperature: 300° C. to 650° C.; reaction pressure: 100 kPa to 500 kPa; and bed density: 150 kg/m$^3$ to 800 kg/m$^3$.

According to a fourth aspect of the present application, a method for preparing low-carbon olefins from an oxygen-containing compound is also provided, including the method for on-line modification of a DMTO catalyst described above.

Optionally, the method may further include: feeding a coke control product gas into a gas-solid separation zone of a methanol conversion reactor; and feeding a coke controlled catalyst into a reaction zone II of the methanol conversion reactor.

Optionally, in the reaction zone II, a raw material with an oxygen-containing compound may contact and react with the coke controlled catalyst to generate a stream A with low-carbon olefins and a spent catalyst.

Optionally, the stream A may be separated into a gas-phase stream B and a solid-phase stream C after being subjected to gas-solid separation in a gas-solid separation zone II of the methanol conversion reactor; the gas-phase stream B may enter a methanol conversion reactor gas collection chamber; the solid-phase stream C may enter a spent catalyst zone; and the gas-phase stream B may include the low-carbon olefins, and the solid-phase stream C may include the spent catalyst.

Optionally, a spent catalyst zone fluidizing gas may be fed into the spent catalyst zone; the spent catalyst zone fluidizing gas and a coke control product gas may be mixed and carry a part of the spent catalyst to produce a stream D; the stream D may be separated into a gas-phase stream E and a solid-phase stream F after being subjected to gas-solid separation; the gas-phase stream E may enter the methanol conversion reactor gas collection chamber; the solid-phase stream F may enter the spent catalyst zone; the gas-phase stream E may be a mixed gas of the spent catalyst zone fluidizing gas and the coke control product gas; and the solid-phase stream F may be the spent catalyst.

Optionally, the gas-phase stream B and the gas-phase stream E may be mixed in the methanol conversion reactor gas collection chamber to produce a product gas, and the product gas may enter a downstream working section through a product gas delivery pipe.

Optionally, a part of the spent catalyst in the spent catalyst zone may be returned to a bottom of the reaction zone II through a spent catalyst circulation pipe; and the remaining part of the spent catalyst may be discharged through a spent catalyst inclined pipe.

Optionally, the spent catalyst discharged through the spent catalyst inclined pipe may be fed into a regenerator; and a regeneration gas may be fed into the regenerator to contact and react with the spent catalyst to obtain a stream G with a flue gas and a regenerated catalyst.

Optionally, the stream G may be subjected to gas-solid separation; a separated flue gas may enter a regenerator gas collection chamber, and then enter a downstream flue gas treatment system through a flue gas delivery pipe; and a separated regenerated catalyst may be stripped and cooled, and then enter a coke control reactor.

Specifically, the separated regenerated catalyst may enter the riser reactor for stripping and cooling, and then may be fed into the bed reactor from the riser reactor.

Optionally, the oxygen-containing compound may include methanol and/or dimethyl ether (DME).

Optionally, a coke content in the spent catalyst may be 9 wt % to 13 wt %.

Optionally, the spent catalyst zone fluidizing gas may include nitrogen and/or water vapor.

Optionally, the regeneration gas may include 0 wt % to 100 wt % of air, 0 wt % to 50 wt % of oxygen, 0 wt % to 50 wt % of nitrogen, and 0 wt % to 50 wt % of water vapor; and contents of the air, the oxygen, the nitrogen, and the water vapor may not be simultaneously zero.

Optionally, process operating conditions of the reaction zone II of the methanol conversion reactor may be as follows: apparent gas linear velocity: 0.5 m/s to 7.0 m/s; reaction temperature: 350° C. to 550° C.; reaction pressure: 100 kPa to 500 kPa; and bed density: 100 kg/m$^3$ to 500 kg/m$^3$.

Optionally, process operating conditions of the spent catalyst zone of the methanol conversion reactor may be as follows: apparent gas linear velocity: 0.1 m/s to 1.0 m/s; reaction temperature: 350° C. to 550° C.; reaction pressure: 100 kPa to 500 kPa; and bed density: 200 kg/m$^3$ to 800 kg/m$^3$.

Optionally, process operating conditions of the regenerator may be as follows: apparent gas linear velocity: 0.5 m/s to 2.0 m/s; regeneration temperature: 600° C. to 750° C.; regeneration pressure: 100 kPa to 500 kPa; and bed density: 150 kg/m$^3$ to 700 kg/m$^3$.

In the present application, the "coke content" refers to a mass ratio of the coke species to the coke controlled catalyst.

Subscripts in $C_4$-$C_6$ each represent the number of carbon atoms in a corresponding group, for example, $C_4$-$C_6$ hydrocarbon compounds represent hydrocarbon compounds with 4 to 6 carbon atoms.

In the present application, when the unit consumption of production is expressed, a mass of DME in the oxygen-containing compound is equivalently converted into a mass of methanol based on a mass of the element C, and a unit of the unit consumption of production is ton of methanol/ton of low-carbon olefins.

In the method of the present application, the unit consumption of production may be 2.50 to 2.60 tons of methanol/ton of low-carbon olefins.

The riser reactor is similar to a plug flow reactor (PFR). Therefore, when the riser reactor is used for a coke control treatment of a catalyst, a narrow coke content distribution can be obtained. A residence time of a catalyst in the riser reactor is short, generally 1 second to 20 seconds. Therefore, it is difficult to greatly increase a coke content in a regenerated catalyst by treating the catalyst only with the riser reactor. The coke control reactor in the present application includes a riser reactor and a bed reactor. On the one hand, a catalyst with a narrow coke content distribution can be obtained through the advantages of the riser reactor; and on the other hand, the bed reactor is used to further increase a coke content in the catalyst and improve the selectivity for low-carbon olefins. A main feature of the bed reactor in the present application is that a perforated plate is arranged to inhibit the back-mixing of a catalyst among beds and improve the uniformity of coke distribution in the catalyst. The catalyst first enters an upper layer of the bed reactor from the riser reactor, gradually flows downward to a lower layer, and then enters the reaction zone II of the methanol conversion reactor from the lower layer.

Possible beneficial effects of the present application:

(1) The coke control reactor in the present application can control the conversion and generation of coke species in a catalyst. On the one hand, inactive large-molecule coke species remaining in a regenerated catalyst are converted into small-molecule coke species; and on the other hand, a riser reactor raw material and a bed reactor raw material can also enter the catalyst to generate highly-active small-molecule coke species, and the small-molecule coke species are mainly polymethylbenzene and polymethylnaphthalene, which can improve the selectivity for ethylene.

(2) With the method for on-line modification of a DMTO catalyst through a coke control reaction in the present application, a coke controlled catalyst with high coke content, narrow coke content distribution, and polymethylbenzene and polymethylnaphthalene as main coke species components can be obtained, that is, the regenerated catalyst with low selectivity for low-carbon olefins is converted into a coke controlled catalyst with high selectivity for low-carbon olefins.

(3) The regenerated catalyst in the present application can be directly used in the process of preparing low-carbon olefins from an oxygen-containing compound without a coke control treatment, and in this case, the selectivity for low-carbon olefins in an obtained product gas is 80 wt % to 83 wt %. When the regenerated catalyst in the present application is subjected to a coke control treatment and then used in the process of preparing low-carbon olefins from an oxygen-containing compound, the selectivity for low-carbon olefins in an obtained product gas is 92 wt % to 96 wt %.

(4) The methanol conversion reactor in the present application adopts a composite fluidized bed reactor including a fast fluidized bed zone and a bubbling fluidized bed zone. The fast fluidized bed zone is a reaction zone, which can obtain a high methanol flux, increase a methanol treatment capacity per unit volume of the device, and make a methanol weight hourly space velocity (WHSV) reach 5 $h^{-1}$ to 20 $h^{-1}$. The bubbling fluidized bed zone is a spent catalyst zone, which is configured to reduce a temperature of a spent catalyst, deliver a low-temperature spent catalyst to the reaction zone, increase a bed density of the reaction zone, and control a bed temperature of the reaction zone. When the apparent gas linear velocity is 0.5 m/s to 7.0 m/s, a corresponding bed density is 500 $kg/m^3$ to 100 $kg/m^3$.

(5) The methanol conversion reactor in the present application adopts a structure in which the first gas-solid separation unit of the methanol conversion reactor is directly connected to the delivery pipe, which realizes the rapid separation of a low-carbon olefin-containing gas and a spent catalyst in the stream A, and avoids that low-carbon olefins further react under the action of the spent catalyst to generate hydrocarbon by-products with a large molecular weight.

Figure 1:
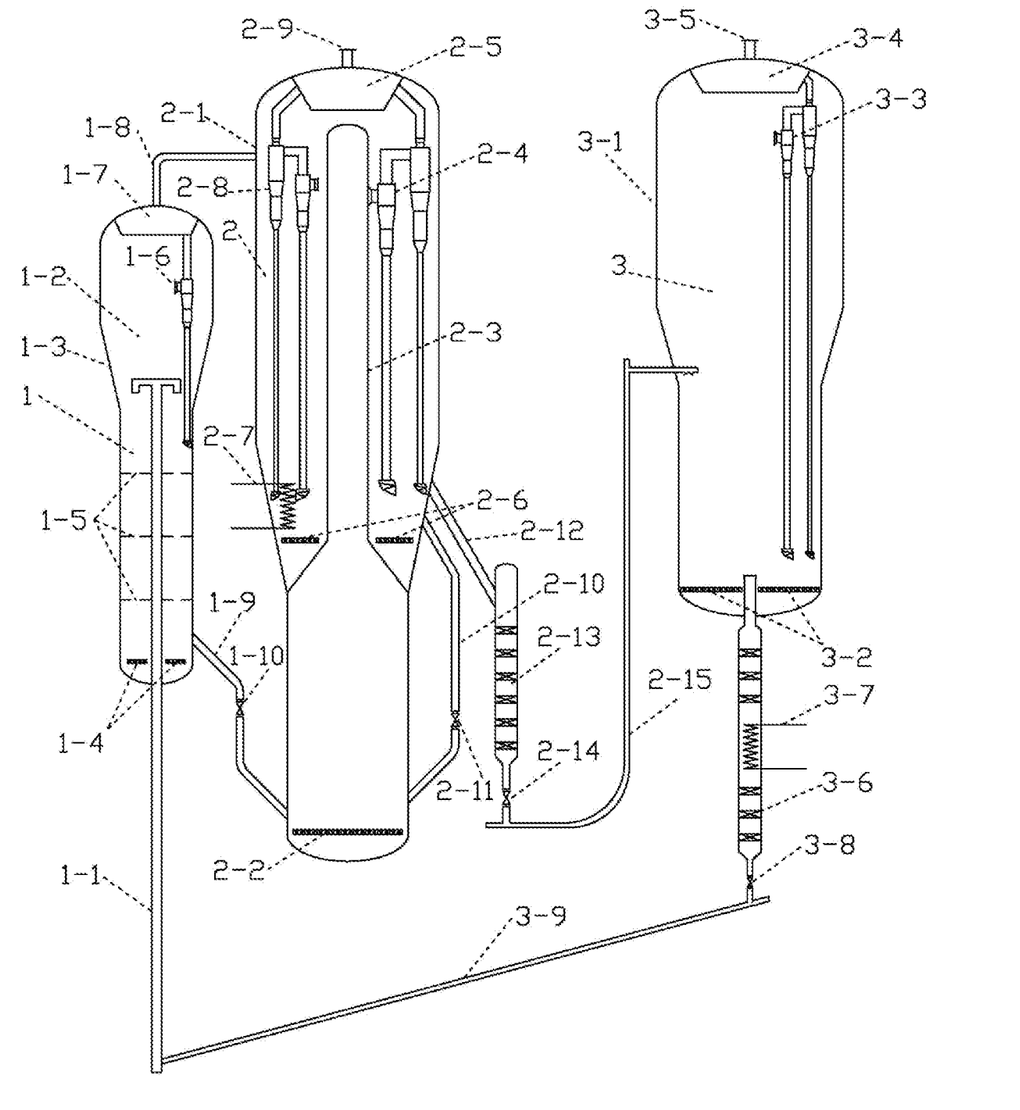
The FIGURE is a schematic structural diagram of a DMTO device for preparing low-carbon olefins from an oxygen-containing compound according to an embodiment of the present application.

LIST OF REFERENCE NUMERALS 1 represents a coke control reactor; 1-1 represents a riser reactor; 1-2 represents a bed reactor; 1-3 represents a bed reactor shell; 1-4 represents a bed reactor distributor; 1-5 represents a perforated plate; 1-6 represents a bed reactor gas-solid cyclone separator; 1-7 represents a bed reactor gas collection chamber; 1-8 represents a coke control product gas delivery pipe; 1-9 represents a coke controlled catalyst delivery pipe; 1-10 represents a coke controlled catalyst slide valve;

2 represents a methanol conversion reactor; 2-1 represents a methanol conversion reactor shell; 2-2 represents a methanol conversion reactor distributor; 2-3 represents a delivery pipe; 2-4 represents a first gas-solid separation unit of the methanol conversion reactor; 2-5 represents a methanol conversion reactor gas collection chamber; 2-6 represents a spent catalyst zone gas distributor; 2-7 represents a methanol conversion reactor cooler; 2-8 represents a second gas-solid separation unit of the methanol conversion reactor; 2-9 represents a product gas delivery pipe; 2-10 represents a spent catalyst circulation pipe; 2-11 represents a spent catalyst circulation slide valve; 2-12 represents a spent catalyst inclined pipe; 2-13 represents a methanol conversion reactor stripper; 2-14 represents a spent catalyst slide valve; 2-15 represents a spent catalyst delivery pipe; 3 represents a regenerator;

3-1 represents a regenerator shell; 3-2 represents a regenerator distributor; 3-3 represents a regenerator gas-solid separation unit; 3-4 represents a regenerator gas collection chamber; 3-5 represents a flue gas delivery pipe; 3-6 represents a regenerator stripper; and 3-7 represents a regenerator cooler; 3-8 represents a regenerated catalyst slide valve; 3-9 represents a regenerated catalyst inclined pipe.

DETAILED DESCRIPTION OF THE EMBODIMENTS

The present application will be described in detail below with reference to examples, but the present application is not limited to these examples.

A major characteristic of a DMTO catalyst is that the low-carbon olefin selectivity in a methanol conversion process increases with the increase of a coke content in the catalyst. The low-carbon olefins mentioned in the present application refer to ethylene and propylene.

The applicants have found through research that main factors affecting the activity of a DMTO catalyst and the selectivity of low-carbon olefins include coke content, coke content distribution, and coke species in the catalyst. Under the same average coke content in catalysts, the narrower the coke content distribution, the higher the selectivity and activity of low-carbon olefins. Coke species in a catalyst may include polymethyl aromatic hydrocarbons, polymethyl cycloalkanes, and the like, where polymethylbenzene and polymethylnaphthalene can promote the formation of ethylene. Therefore, the control of the coke content, coke content distribution, and coke species in a catalyst is the key to control the activity of the DMTO catalyst and improve the selectivity of low-carbon olefins.

In order to improve the performance of a DMTO catalyst, the present application provides a method for on-line modification of a DMTO catalyst through a coke control reaction, including the following steps:
a) a regenerated catalyst is delivered to a coke control reactor;
b) a coke control raw material including hydrogen, methane, ethane, ethylene, propane, propylene, butane, butene, pentane, pentene, hexane, hexene, methanol, ethanol, and water is delivered to the coke control reactor;
c) the coke control raw material contacts and reacts with the regenerated catalyst in the coke control reactor, such that the coke control raw material is coked on the regenerated catalyst, where a coked catalyst is called a coke controlled catalyst; a coke content in the coke controlled catalyst is 4 wt % to 9 wt %, and a quartile deviation of coke content distribution is less than 1 wt %; coke species include polymethylbenzene and polymethylnaphthalene, and a total mass of the polymethylbenzene and the polymethylnaphthalene accounts for greater than or equal to 70 wt % of a total mass of coke; and a mass of coke species with a molecular weight greater than 184 accounts for less than or equal to 25 wt % of the total mass of coke; and
d) the coke controlled catalyst is delivered to a methanol conversion reactor.

The regenerated catalyst may be a DMTO catalyst with a coke content of less than or equal to 3 wt %, and an active component of the DMTO catalyst may be an SAPO-34 molecular sieve.

The coke control raw material may be composed of 0 wt % to 20 wt % of hydrogen, 0 wt % to 50 wt % of methane, 0 wt % to 50 wt % of ethane, 0 wt % to 20 wt % of ethylene, 0 wt % to 50 wt % of propane, 0 wt % to 20 wt % of propylene, 0 wt % to 90 wt % of butane, 0 wt % to 90 wt % of butene, 0 wt % to 90 wt % of pentane, 0 wt % to 90 wt % of pentene, 0 wt % to 90 wt % of hexane, 0 wt % to 90 wt % of hexene, 0 wt % to 50 wt % of methanol, 0 wt % to 50 wt % of ethanol, and 0 wt % to 50 wt % of water, and a total content of methanol, ethanol, and water may be greater than or equal to 10 wt %.

A reaction temperature of the coke control reaction may be 300° C. to 700° C.

In the present application, both the bed reactor raw material and the riser reactor raw material are coke control raw materials.

According to an aspect of the present application, a method for preparing low-carbon olefins from an oxygen-containing compound that includes the method for on-line modification of a DMTO catalyst through a coke control reaction described above, and a device used thereby are provided. The device includes a coke control reactor (1), a methanol conversion reactor (2), and a regenerator (3).

A coke control reactor (1) for on-line modification of a DMTO catalyst is provided, where the coke control reactor (1) includes a riser reactor (1-1) and a bed reactor (1-2); the bed reactor (1-2) includes a bed reactor shell (1-3), a bed reactor distributor (1-4), a perforated plate (1-5), a bed reactor gas-solid cyclone separator (1-6), a bed reactor gas collection chamber (1-7), a coke control product gas delivery pipe (1-8), a coke controlled catalyst delivery pipe (1-9), and a coke controlled catalyst slide valve (1-10);

the bed reactor (1-2) is divided into a reaction zone, a transition zone, and a gas-solid separation zone from bottom to top; the riser reactor (1-1) penetrates through the bed reactor shell (1-3), and is partially located below the bed reactor (1-2) and partially located in the bed reactor (1-2); the bed reactor distributor (1-4) is located at a bottom of the reaction zone, and n perforated plates (1-5) are arranged in the reaction zone, where $0 \leq n \leq 9$;

the bed reactor gas-solid cyclone separator (1-6) is located in the gas-solid separation zone, an inlet of the bed reactor gas-solid cyclone separator (1-6) is formed in the gas-solid separation zone, a catalyst outlet of the bed reactor gas-solid cyclone separator (1-6) is formed in the reaction zone, and a gas outlet of the bed reactor gas-solid cyclone separator (1-6) is connected to a bed reactor gas collection chamber (1-7);

the bed reactor gas collection chamber (1-7) is located at a top of the bed reactor (1-2); an inlet of the coke control product gas delivery pipe (1-8) is connected to the bed reactor gas collection chamber (1-7), and an outlet of the coke control product gas delivery pipe (1-8) is connected to an upper part of the methanol conversion reactor (2);

the coke controlled catalyst slide valve (1-10) is arranged in the coke controlled catalyst delivery pipe (1-9); and an inlet of the coke controlled catalyst delivery pipe (1-9) is connected to a lower part of the reaction zone, and an outlet of the coke controlled catalyst delivery pipe (1-9) is connected to a lower part of the methanol conversion reactor (2).

In a preferred embodiment, the perforated plate may have a porosity of 1% to 30%.

A methanol conversion reactor (2) for preparing low-carbon olefins through methanol conversion, where the methanol conversion reactor (2) includes a methanol conversion reactor shell (2-1), a methanol conversion reactor distributor (2-2), a delivery pipe (2-3), a first gas-solid separation unit (2-4) of the methanol conversion reactor, a methanol conversion reactor gas collection chamber (2-5), a spent catalyst zone gas distributor (2-6), a methanol conversion reactor cooler (2-7), a second gas-solid separation unit (2-8) of the methanol conversion reactor, a product gas delivery pipe (2-9), a spent catalyst circulation pipe (2-10), a spent catalyst circulation slide valve (2-11), a spent catalyst inclined pipe (2-12), a methanol conversion reactor stripper (2-13), a spent catalyst slide valve (2-14), and a spent catalyst delivery pipe (2-15);

a lower part of the methanol conversion reactor (2) is a reaction zone, a middle part thereof is a spent catalyst zone, and an upper part thereof is a gas-solid separation zone; the methanol conversion reactor distributor (2-2) is located at a bottom of the reaction zone of the methanol conversion reactor (2); the delivery pipe (2-3) is located in central zones of the middle and upper parts of the methanol conversion reactor (2); a bottom end of the delivery pipe (2-3) is connected to a top end of the reaction zone, and an upper part of the delivery pipe (2-3) is connected to an inlet of the first gas-solid separation unit (2-4) of the methanol conversion reactor; the first gas-solid separation unit (2-4) of the methanol conversion reactor is located in the gas-solid separation zone of the methanol conversion reactor (2); and a gas outlet of the first gas-solid separation unit (2-4) of the methanol conversion reactor is connected to the methanol conversion reactor gas collection chamber (2-5), and a catalyst outlet of the first gas-solid separation unit (2-4) of the methanol conversion reactor is formed in the spent catalyst zone;

the spent catalyst zone gas distributor (2-6) is located at a bottom of the spent catalyst zone, the methanol conversion reactor cooler (2-7) is located in the spent catalyst zone, and the second gas-solid separation unit (2-8) of the methanol conversion reactor is located in the gas-solid separation zone of the methanol conversion reactor (2); an inlet of the second gas-solid separation unit (2-8) of the methanol conversion reactor is formed in the gas-solid separation zone of the methanol conversion reactor (2), a gas outlet of the second gas-solid separation unit (2-8) of the methanol conversion reactor is connected to the methanol conversion reactor gas collection chamber (2-5), and a catalyst outlet of the second gas-solid separation unit (2-8) of the methanol conversion reactor is formed in the spent catalyst zone; the methanol conversion reactor gas collection chamber (2-5) is located at a top of the methanol conversion reactor (2), and the product gas delivery pipe (2-9) is connected to a top of the methanol conversion reactor gas collection chamber (2-5);

an inlet of the spent catalyst circulation pipe (2-10) is connected to the spent catalyst zone, and an outlet of the spent catalyst circulation pipe (2-10) is connected to the bottom of the reaction zone of the methanol conversion reactor (2); the spent catalyst circulation slide valve (2-11) is arranged in the spent catalyst circulation pipe (2-10); an outlet of the coke controlled catalyst delivery pipe (1-9) is connected to the bottom of the reaction zone of the methanol conversion reactor (2), an inlet of the spent catalyst inclined pipe (2-12) is connected to the spent catalyst zone, and an outlet of the spent catalyst inclined pipe (2-12) is connected to an upper part of the methanol conversion reactor stripper (2-13); the methanol conversion reactor stripper (2-13) is arranged outside the methanol conversion reactor shell (2-1); and an inlet of the spent catalyst slide valve (2-14) is connected to a bottom of the methanol conversion reactor stripper (2-13) through a pipeline, an outlet of the spent catalyst slide valve (2-14) is connected to an inlet of the spent catalyst delivery pipe (2-15) through a pipeline, and an outlet of the spent catalyst delivery pipe (2-15) is connected to a middle part of the regenerator (3).

In a preferred embodiment, the first gas-solid separation unit (2-4) of the methanol conversion reactor may adopt one or more sets of gas-solid cyclone separators, and each set of gas-solid cyclone separators may include a first-stage gas-solid cyclone separator and a second-stage gas-solid cyclone separator.

In a preferred embodiment, the second gas-solid separation unit (2-8) of the methanol conversion reactor may adopt one or more sets of gas-solid cyclone separators, and each set of gas-solid cyclone separators may include a first-stage gas-solid cyclone separator and a second-stage gas-solid cyclone separator.

The methanol conversion reactor (2) may be a fluidized bed reactor.

A regenerator (3) for regenerating a catalyst is provided, where the regenerator (3) includes a regenerator shell (3-1), a regenerator distributor (3-2), a regenerator gas-solid separation unit (3-3), a regenerator gas collection chamber (3-4), a flue gas delivery pipe (3-5), a regenerator stripper (3-6), a regenerator cooler (3-7), a regenerated catalyst slide valve (3-8), and a regenerated catalyst inclined pipe (3-9);

the regenerator distributor (3-2) is located at a bottom of the regenerator (3), and the regenerator gas-solid separation unit (3-3) is located at an upper part of the regenerator (3); an inlet of the regenerator gas-solid separation unit (3-3) is formed at an upper part of the regenerator (3), a gas outlet of the regenerator gas-solid separation unit (3-3) is connected to the regenerator gas collection chamber (3-4), and a catalyst outlet of the regenerator gas-solid separation unit (3-3) is formed at a lower part of the regenerator (3); the regenerator gas collection chamber (3-4) is located at a top of the regenerator (3), and the flue gas delivery pipe (3-5) is connected to a top of the regenerator gas collection chamber (3-4);

the regenerator stripper (3-6) is located outside the regenerator shell (3-1), and an inlet pipe of the regenerator stripper (3-6) penetrates through the regenerator shell (3-1) and is opened above the regenerator distributor (3-2); the regenerator cooler (3-7) is located in the regenerator stripper (3-6); and an inlet of the regenerated catalyst slide valve (3-8) is connected to a bottom of the regenerator stripper (3-6) through a pipeline, an outlet of the regenerated catalyst slide valve (3-8) is connected to an inlet of the regenerated catalyst inclined pipe (3-9) through a pipeline, and an outlet of the regenerated catalyst inclined pipe (3-9) is connected to a bottom of the riser reactor (1-1).

In a preferred embodiment, the regenerator gas-solid separation unit (3-3) may adopt one or more sets of gas-solid cyclone separators, and each set of gas-solid cyclone separators may include a first-stage gas-solid cyclone separator and a second-stage gas-solid cyclone separator.

The regenerator (3) may be a fluidized bed reactor.

In the present application, an inner diameter of the transition zone of the coke control reactor gradually increases from bottom to top; in the methanol conversion reactor, an inner diameter of a junction between the reaction zone II and the delivery pipe gradually decreases from bottom to top; and an inner diameter of a junction between the reaction zone II and the spent catalyst zone gradually increases from bottom to top.

Optionally, an inlet of the coke controlled catalyst delivery pipe may be formed above the bed reactor distributor; an outlet of the coke controlled catalyst delivery pipe may be formed above the methanol conversion reactor distributor; an inlet of the spent catalyst circulation pipe may be formed above the spent catalyst zone gas distributor, and an outlet of the spent catalyst circulation pipe may be formed above the methanol conversion reactor distributor; and the spent catalyst inclined pipe may be located above the spent catalyst zone gas distributor.

According to another aspect of the present application, an MTO method including the method for on-line modification of a DMTO catalyst through a coke control reaction is also provided, including the following steps:

a. a riser reactor raw material is fed from a bottom of the riser reactor (1-1), which carries a regenerated catalyst from the regenerated catalyst inclined pipe (3-9) and moves upward into the transition zone of the bed reactor (1-2); a bed reactor raw material is fed from the bed reactor distributor (1-4) into the reaction zone of the bed reactor (1-2); in the riser reactor (1-1) and the bed reactor (1-2), the regenerated catalyst contacts the riser reactor raw material and the bed reactor raw material to allow a chemical reaction to generate a coke controlled catalyst and a coke control product gas; the coke control product gas carrying a part of the coke controlled catalyst enters the bed reactor gas-solid cyclone separator (1-6) to undergo gas-solid separation, and then the coke control product gas enters the gas-solid separation zone of the methanol conversion reactor (2) through the bed reactor gas collection chamber (1-7) and the coke control product gas delivery pipe (1-8); and the coke controlled catalyst enters the reaction zone of the methanol conversion reactor (2) through the coke controlled catalyst delivery pipe (1-9) and the coke controlled catalyst slide valve (1-10);

b. a raw material with an oxygen-containing compound is fed into the reaction zone of the methanol conversion reactor (2) from the methanol conversion reactor distributor (2-2), and contacts the coke controlled catalyst to generate a stream A with low-carbon olefins and a spent catalyst; the stream A enters the first gas-solid separation unit (2-4) of the methanol conversion reactor through the delivery pipe (2-3) to undergo gas-solid separation to obtain a gas-phase stream B and a solid-phase stream C, where the gas-phase stream B is a gas with low-carbon olefins and the solid-phase stream C is a spent catalyst; the gas-phase stream B enters the methanol conversion reactor gas collection chamber (2-5), and the solid-phase stream C enters the spent catalyst zone; a spent catalyst zone fluidizing gas is fed into the spent catalyst zone from the spent catalyst zone gas distributor (2-6) and contacts the spent catalyst, and the spent catalyst zone fluidizing gas and the coke control product gas are mixed and carry a part of the spent catalyst to produce a stream D; the stream D enters the second gas-solid separation unit (2-8) of the methanol conversion reactor to undergo gas-solid separation to obtain a gas-phase stream E and a solid-phase stream F, where the gas-phase stream E is a mixed gas of the spent catalyst zone fluidizing gas and the coke control product gas and the solid-phase stream F is the spent catalyst; the gas-phase stream E enters the methanol conversion reactor gas collection chamber (2-5), and the solid-phase stream F enters the spent catalyst zone; the gas-phase stream B and the gas-phase stream E are mixed in the methanol conversion reactor gas collection chamber (2-5) to produce a product gas, and the product gas enters a downstream working section through the product gas delivery pipe (2-9); a part of the spent catalyst in the spent catalyst zone is returned to a bottom of the reaction zone of the methanol conversion reactor (2) through the spent catalyst circulation pipe (2-10) and the spent catalyst circulation slide valve (2-11), and the remaining part of the spent catalyst enters the methanol conversion reactor stripper (2-13) through the spent catalyst inclined pipe (2-12) to undergo stripping, and then enters a middle part of the regenerator (3) through the spent catalyst slide valve (2-14) and the spent catalyst delivery pipe (2-15); and c. a regeneration gas is fed from the regenerator distributor (3-2) to the bottom of the regenerator (3), and in the regenerator, the regeneration gas contacts the spent catalyst to allow a chemical reaction, such that a part of coke in the spent catalyst is burned and eliminated to generate a stream G with a flue gas and a regenerated catalyst; the stream G enters the regenerator gas-solid separation unit (3-3) to undergo gas-solid separation to obtain a flue gas and a regenerated catalyst; the flue gas enters the regenerator gas collection chamber (3-4), and then enters a downstream flue gas treatment system through the flue gas delivery pipe (3-5); the regenerated catalyst is returned to the bottom of the regenerator (3); and the regenerated catalyst in the regenerator (3) enters the regenerator stripper (3-6) to be stripped and cooled, and then enters the coke control reactor (1) through the regenerated catalyst slide valve (3-8) and the regenerated catalyst inclined pipe (3-9).

In a preferred embodiment, the method of the present application may be implemented using the above-mentioned device including a coke control reactor (1), a methanol conversion reactor (2), and a regenerator (3).

In a preferred embodiment, a riser reactor raw material in the method may be composed of 0 wt % to 20 wt % of hydrogen, 0 wt % to 50 wt % of methane, 0 wt % to 50 wt % of ethane, 0 wt % to 20 wt % of ethylene, 0 wt % to 50 wt % of propane, 0 wt % to 20 wt % of propylene, 0 wt % to 90 wt % of butane, 0 wt % to 90 wt % of butene, 0 wt % to 90 wt % of pentane, 0 wt % to 90 wt % of pentene, 0 wt % to 90 wt % of hexane, 0 wt % to 90 wt % of hexene, 0 wt % to 50 wt % of methanol, 0 wt % to 50 wt % of ethanol, and 0 wt % to 50 wt % of water, and a total content of methanol, ethanol, and water may be greater than or equal to 10 wt %.

In a preferred embodiment, a bed reactor raw material in the method may be composed of 0 wt % to 20 wt % of hydrogen, 0 wt % to 50 wt % of methane, 0 wt % to 50 wt % of ethane, 0 wt % to 20 wt % of ethylene, 0 wt % to 50 wt % of propane, 0 wt % to 20 wt % of propylene, 0 wt % to 90 wt % of butane, 0 wt % to 90 wt % of butene, 0 wt % to 90 wt % of pentane, 0 wt % to 90 wt % of pentene, 0 wt % to 90 wt % of hexane, 0 wt % to 90 wt % of hexene, 0 wt % to 50 wt % of methanol, 0 wt % to 50 wt % of ethanol, and 0 wt % to 50 wt % of water, and a total content of methanol, ethanol, and water may be greater than or equal to 10 wt %.

In a preferred embodiment, the oxygen-containing compound in the method may be one from the group consisting of methanol, DME, and a mixture of methanol and DME.

In a preferred embodiment, the spent catalyst zone fluidizing gas in the method may be one from the group consisting of nitrogen, water vapor, and a mixture of nitrogen and water vapor.

In a preferred embodiment, the regeneration gas in the method may be 0 wt % to 100 wt % air, 0 wt % to 50 wt % oxygen, 0 wt % to 50 wt % nitrogen, and 0 wt % to 50 wt % water vapor.

In a preferred embodiment, an active component of the catalyst may be an SAPO-34 molecular sieve.

In a preferred embodiment, a coke content in the regenerated catalyst may be less than or equal to 3 wt %.

In a preferred embodiment, a coke content in the coke controlled catalyst may be 4 wt % to 9 wt %, and a quartile deviation of coke content distribution may be less than 1 wt %; coke species may include polymethylbenzene and polymethylnaphthalene, and a total mass of the polymethylbenzene and the polymethylnaphthalene may account for greater than or equal to 70 wt % of a total mass of coke; and a mass of coke species with a molecular weight greater than 184 may account for less than or equal to 25 wt % of the total mass of coke.

In a preferred embodiment, a coke content in the spent catalyst may be 9 wt % to 13 wt %, and further preferably, the coke content in the spent catalyst may be 10 wt % to 12 wt %.

In a preferred embodiment, process operating conditions of the riser reactor (1-1) may be as follows: apparent gas linear velocity: 3 m/s to 10 m/s; reaction temperature: 400° C. to 700° C.; reaction pressure: 100 kPa to 500 kPa; and bed density: 10 kg/m$^3$ to 150 kg/m$^3$.

In a preferred embodiment, process operating conditions of the reaction zone of the bed reactor (1-2) may be as follows: apparent gas linear velocity: 0.1 m/s to 1.0 m/s; reaction temperature: 300° C. to 650° C.; reaction pressure: 100 kPa to 500 kPa; and bed density: 150 kg/m$^3$ to 800 kg/m$^3$.

In a preferred embodiment, process operating conditions of the reaction zone of the methanol conversion reactor (2) may be as follows: apparent gas linear velocity: 0.5 m/s to 7.0 m/s; reaction temperature: 350° C. to 550° C.; reaction pressure: 100 kPa to 500 kPa; and bed density: 100 kg/m$^3$ to 500 kg/m$^3$.

In a preferred embodiment, process operating conditions of the spent catalyst zone of the methanol conversion reactor (2) may be as follows: apparent gas linear velocity: 0.1 m/s to 1.0 m/s; reaction temperature: 350° C. to 550° C.; reaction pressure: 100 kPa to 500 kPa; and bed density: 200 kg/m$^3$ to 800 kg/m$^3$.

In a preferred embodiment, process operating conditions of the regenerator (3) may be as follows: apparent gas linear velocity: 0.5 m/s to 2.0 m/s; regeneration temperature: 600° C. to 750° C.; regeneration pressure: 100 kPa to 500 kPa; and bed density: 150 kg/m$^3$ to 700 kg/m$^3$.

In the method of the present application, the product gas may be composed of 40 wt % to 55 wt % of ethylene, 37 wt % to 53 wt % of propylene, less than or equal to 4 wt % of $C_4$-$C_6$ hydrocarbon compounds, and less than or equal to 4 wt % of other components; and the other components may be methane, ethane, propane, hydrogen, CO, $CO_2$, and the like, and the total selectivity of ethylene and propylene in the product gas may be 92 wt % to 96 wt %.

Example 1

In this example, the device shown in the FIGURE is adopted, where there is no perforated plate in the bed reactor.

In this example, the riser reactor raw material is a mixture of 6 wt % of butane, 81 wt % of butene, 2 wt % of methanol, and 11 wt % of water; the bed reactor raw material is a mixture of 6 wt % of butane, 81 wt % of butene, 2 wt % of methanol, and 11 wt % of water; the oxygen-containing compound is methanol; the spent catalyst zone fluidizing gas is nitrogen; the regeneration gas is air; an active component in the catalyst is an SAPO-34 molecular sieve; a coke content in the regenerated catalyst is about 3 wt %; a coke content in the coke controlled catalyst is about 6 wt %, where a total mass of polymethylbenzene and polymethylnaphthalene accounts for about 82 wt % of a total mass of coke, a mass of coke species with a molecular weight greater than 184 accounts for about 5 wt % of a total mass of coke, and a quartile deviation of coke content distribution in the coke controlled catalyst is about 0.9 wt %; a coke content in the spent catalyst is about 12 wt %; process operating conditions of the riser reactor (1-1) are as follows: apparent gas linear velocity: 10.0 m/s, reaction temperature: 700° C., reaction pressure: 100 kPa, and bed density: 10 kg/m$^3$; process operating conditions of the reaction zone of the bed reactor (1-2) are as follows: apparent gas linear velocity: about 0.3 m/s, reaction temperature: about 650° C., reaction pressure: about 100 kPa, and bed density: about 600 kg/m$^3$; process operating conditions of the reaction zone of the methanol conversion reactor (2) are as follows: apparent gas linear velocity: about 7.0 m/s, reaction temperature: about 550° C., reaction pressure: about 100 kPa, and bed density: about 100 kg/m$^3$; process operating conditions of the spent catalyst zone of the methanol conversion reactor (2) are as follows: apparent gas linear velocity: about 1.0 m/s, reaction temperature: about 550° C., reaction pressure: about 100 kPa, and bed density: about 200 kg/m$^3$; and process operating conditions of the regenerator (3) are as follows: apparent gas linear velocity: about 0.5 m/s, regeneration temperature: about 750° C., regeneration pressure: about 100 kPa, and bed density: about 700 kg/m$^3$.

In this example, a WHSV of the oxygen-containing compound in the methanol conversion reactor is about 20 the product gas is composed of 55 wt % of ethylene, 37 wt % of propylene, 4 wt % of $C_4$-$C_6$ hydrocarbon compounds, and 4 wt % of other components, where the other components include methane, ethane, propane, hydrogen, CO, $CO_2$, and the like; and the unit consumption of production is 2.60 tons of methanol/ton of low-carbon olefins.

Example 2

In this example, the device shown in the FIGURE is adopted, where there are 4 perforated plates in the bed reactor, and the perforated plates have a porosity of 30%.

In this example, the riser reactor raw material is a mixture of 22 wt % of methane, 24 wt % of ethane, 3 wt % of ethylene, 28 wt % of propane, 4 wt % of propylene, 7 wt % of hydrogen, and 12 wt % of water; the bed reactor raw material is a mixture of 22 wt % of methane, 24 wt % of ethane, 3 wt % of ethylene, 28 wt % of propane, 4 wt % of propylene, 7 wt % of hydrogen, and 12 wt % of water; the oxygen-containing compound is a mixture of 82 wt % of methanol and 18 wt % of DME; the spent catalyst zone fluidizing gas is water vapor; the regeneration gas is a mixture of 50 wt % of air and 50 wt % of water vapor; an active component in the catalyst is an SAPO-34 molecular sieve; a coke content in the regenerated catalyst is about 1 wt %; a coke content in the coke controlled catalyst is about 4 wt %, where a total mass of polymethylbenzene and polymethylnaphthalene accounts for about 76 wt % of a total mass of coke, a mass of coke species with a molecular weight greater than 184 accounts for about 15 wt % of a total mass of coke, and a quartile deviation of coke content distribution in the coke controlled catalyst is about 0.5 wt %; a coke content in the spent catalyst is about 9 wt %; process operating conditions of the riser reactor (1-1) are as follows: apparent gas linear velocity: 3.0 m/s, reaction temperature: 400° C., reaction pressure: 500 kPa, and bed density: 150 kg/m$^3$; process operating conditions of the reaction zone of the bed reactor (1-2) are as follows: apparent gas linear velocity: about 0.1 m/s, reaction temperature: about 300° C., reaction pressure: about 500 kPa, and bed density: about 800 kg/m$^3$; process operating conditions of the reaction zone of the methanol conversion reactor (2) are as follows: apparent gas linear velocity: about 0.5 m/s, reaction temperature: about 350° C., reaction pressure: about 500 kPa, and bed density: about 500 kg/m$^3$; process operating conditions of the spent catalyst zone of the methanol conversion reactor (2) are as follows: apparent gas linear velocity: about 0.1 m/s, reaction temperature: about 350° C., reaction pressure: about 500 kPa, and bed density: about 800 kg/m$^3$; and process operating conditions of the regenerator (3) are as follows: apparent gas linear velocity: about 2.0 m/s, regeneration temperature: about 600° C., regeneration pressure: about 500 kPa, and bed density: about 150 kg/m$^3$.

In this example, a WHSV of the oxygen-containing compound in the methanol conversion reactor is about 5 the product gas is composed of 40 wt % of ethylene, 53 wt % of propylene, 4 wt % of $C_4$-$C_6$ hydrocarbon compounds, and 3 wt % of other components, where the other components include methane, ethane, propane, hydrogen, CO, $CO_2$, and the like; and the unit consumption of production is 2.58 tons of methanol/ton of low-carbon olefins.

Example 3

In this example, the device shown in the FIGURE is adopted, where there are 4 perforated plates in the bed reactor, and the perforated plates have a porosity of 1%.

In this example, the riser reactor raw material is a mixture of 1 wt % of propane, 1 wt % of propylene, 3 wt % of butane, 51 wt % of butene, 3 wt % of pentane, 22 wt % of pentene, 1 wt % of hexane, 7 wt % of hexene, 2 wt % of methanol, and 9 wt % of water; the bed reactor raw material is a mixture of 1 wt % of propane, 1 wt % of propylene, 3 wt % of butane, 51 wt % of butene, 3 wt % of pentane, 22 wt % of pentene, 1 wt % of hexane, 7 wt % of hexene, 2 wt % of methanol, and 9 wt % of water; the oxygen-containing compound is DME; the spent catalyst zone fluidizing gas is a mixture of 5 wt % of nitrogen and 95 wt % of water vapor; the regeneration gas is a mixture of 50 wt % of air and 50 wt % of oxygen; an active component in the catalyst is an SAPO-34 molecular sieve; a coke content in the regenerated catalyst is about 2 wt %; a coke content in the coke controlled catalyst is about 5 wt %, where a total mass of polymethylbenzene and polymethylnaphthalene accounts for about 79 wt % of a total mass of coke, a mass of coke species with a molecular weight greater than 184 accounts for about 10 wt % of a total mass of coke, and a quartile deviation of coke content distribution in the coke controlled catalyst is about 0.5 wt %; a coke content in the spent catalyst is about 11 wt %; process operating conditions of the riser reactor (1-1) are as follows: apparent gas linear velocity: 6.0 m/s, reaction temperature: 600° C., reaction pressure: 300 kPa, and bed density: 80 kg/m$^3$; process operating conditions of the reaction zone of the bed reactor (1-2) are as follows: apparent gas linear velocity: about 0.4 m/s, reaction temperature: about 550° C., reaction pressure: about 300 kPa, and bed density: about 500 kg/m$^3$; process operating conditions of the reaction zone of the methanol conversion reactor (2) are as follows: apparent gas linear velocity: about 3.0 m/s, reaction temperature: about 450° C., reaction pressure: about 300 kPa, and bed density: about 230 kg/m$^3$; process operating conditions of the spent catalyst zone of the methanol conversion reactor (2) are as follows: apparent gas linear velocity: about 0.2 m/s, reaction temperature: about 450° C., reaction pressure: about 300 kPa, and bed density: about 600 kg/m$^3$; and process operating conditions of the regenerator (3) are as follows: apparent gas linear velocity: about 1.0 m/s, regeneration temperature: about 680° C., regeneration pressure: about 300 kPa, and bed density: about 360 kg/m$^3$.

In this example, a WHSV of the oxygen-containing compound in the methanol conversion reactor is about 15 the product gas is composed of 50 wt % of ethylene, 45 wt % of propylene, 3 wt % of $C_4$-$C_6$ hydrocarbon compounds, and 2 wt % of other components, where the other components include methane, ethane, propane, hydrogen, CO, $CO_2$, and the like; and the unit consumption of production is 2.53 tons of methanol/ton of low-carbon olefins.

Example 4

In this example, the device shown in the FIGURE is adopted, where there are 9 perforated plates in the bed reactor, and the perforated plates have a porosity of 5%.

In this example, the riser reactor raw material is a mixture of 5 wt % of butane, 72 wt % of butene, 8 wt % of methanol, and 15 wt % of water; the bed reactor raw material is a mixture of 5 wt % of butane, 72 wt % of butene, 8 wt % of methanol, and 15 wt % of water; the oxygen-containing compound is methanol; the spent catalyst zone fluidizing gas is a mixture of 73 wt % of nitrogen and 27 wt % of water vapor; the regeneration gas is a mixture of 50 wt % of air and 50 wt % of nitrogen; an active component in the catalyst is an SAPO-34 molecular sieve; a coke content in the regenerated catalyst is about 2 wt %; a coke content in the coke controlled catalyst is about 9 wt %, where a total mass of polymethylbenzene and polymethylnaphthalene accounts for about 71 wt % of a total mass of coke, a mass of coke species with a molecular weight greater than 184 accounts for about 25 wt % of a total mass of coke, and a quartile deviation of coke content distribution in the coke controlled catalyst is about 0.2 wt %; a coke content in the spent catalyst is about 13 wt %; process operating conditions of the riser reactor (1-1) are as follows: apparent gas linear velocity: 4.0 m/s, reaction temperature: 550° C., reaction pressure: 200 kPa, and bed density: 120 kg/m$^3$; process operating conditions of the reaction zone of the bed reactor (1-2) are as follows: apparent gas linear velocity: about 1.0 m/s, reaction temperature: about 500° C., reaction pressure: about 200 kPa, and bed density: about 150 kg/m$^3$; process operating conditions of the reaction zone of the methanol conversion reactor (2) are as follows: apparent gas linear velocity: about 4.0 m/s, reaction temperature: about 500° C., reaction pressure: about 200 kPa, and bed density: about 160 kg/m$^3$; process operating conditions of the spent catalyst zone of the methanol conversion reactor (2) are as follows: apparent gas linear velocity: about 0.5 m/s, reaction temperature: about 500° C., reaction pressure: about 200 kPa, and bed density: about 300 kg/m$^3$; and process operating conditions of the regenerator (3) are as follows: apparent gas linear velocity: about 1.5 m/s, regeneration temperature: about 700° C., regeneration pressure: about 200 kPa, and bed density: about 280 kg/m$^3$.

In this example, a WHSV of the oxygen-containing compound in the methanol conversion reactor is about 11 the product gas is composed of 52 wt % of ethylene, 44 wt % of propylene, 2 wt % of $C_4$-$C_6$ hydrocarbon compounds, and 2 wt % of other components, where the other components include methane, ethane, propane, hydrogen, CO, $CO_2$, and the like; and the unit consumption of production is 2.50 tons of methanol/ton of low-carbon olefins.

Example 5

This example is a comparative example and is different from Example 4 in that, the coke control reaction is not used for on-line modification of the DMTO catalyst; and the raw material fed into the riser reactor and the bed reactor is nitrogen, which is an inert gas and does not change the properties of the regenerated catalyst in the riser reactor and the bed reactor, that is, a catalyst entering the reaction zone II of the methanol conversion reactor is the regenerated catalyst.

In this example, the product gas is composed of 46 wt % of ethylene, 37 wt % of propylene, 12 wt % of $C_4$-$C_6$ hydrocarbon compounds, and 5 wt % of other components, where the other components include methane, ethane, propane, hydrogen, CO, $CO_2$, and the like; and the unit consumption of production is 2.90 tons of methanol/ton of low-carbon olefins.

This comparative example shows that the on-line modification of a DMTO catalyst through a coke control reaction can greatly improve the performance of the catalyst and reduce the unit consumption of production.

The above examples are merely few examples of the present application, and do not limit the present application in any form. Although the present application is disclosed as above with preferred examples, the present application is not limited thereto. Some changes or modifications made by any technical personnel familiar with the profession using the technical content disclosed above without departing from the scope of the technical solutions of the present application are equivalent to equivalent implementation cases and fall within the scope of the technical solutions.

What is claimed is:

1. A reactor, wherein the coke control reactor comprises a riser reactor and a bed reactor;
    the bed reactor comprises a bed reactor shell, and the bed reactor shell encloses a first reaction zone, a transition zone, and a first gas-solid separation zone from bottom to top;
    a bed reactor distributor is arranged in the first reaction zone;
    a coke controlled catalyst delivery pipe is arranged outside the first reaction zone;
    a section of the riser reactor penetrates into the bed reactor and is axially inserted in the bed reactor;
    an outlet end of the riser reactor is located in the transition zone; and
    at least one perforated plate is arranged in the first reaction zone; the at least one perforated plate are axially arranged on a periphery of the riser reactor in sequence, the at least one perforated plate are arranged horizontally, and a periphery of the at least one perforated plate abuts against an inner wall of the bed reactor, such that a stream passes through apertures in the at least one perforated plate.

2. The coke control reactor according to claim 1, wherein
    the outlet end of the riser reactor is located above the at least one perforated plate;
    the bed reactor distributor is located below the at least one perforated plate; and
    the at least one perforated plate has a porosity of 1% to 30%.

3. The coke control reactor according to claim 1, wherein the first gas-solid separation zone is provided with a bed reactor gas-solid separator and a bed reactor gas collection chamber;
    a gas outlet of the bed reactor gas-solid separator communicates with the bed reactor gas collection chamber;
    a catalyst outlet of the bed reactor gas-solid separator is located above the at least one perforated plate;
    the bed reactor gas collection chamber communicates with a coke control product gas delivery pipe located outside the bed reactor;
    the bed reactor distributor is configured to feed a bed reactor raw material, and the bed reactor raw material, based on a weight percentage of 100%, comprises 0 wt % to 20 wt % of hydrogen, 0 wt % to 50 wt % of methane, 0 wt % to 50 wt % of ethane, 0 wt % to 20 wt % of ethylene, 0 wt % to 50 wt % of propane, 0 wt % to 20 wt % of propylene, 0 wt % to 90 wt % of butane, 0 wt % to 90 wt % of butene, 0 wt % to 90 wt % of pentane, 0 wt % to 90 wt % of pentene, 0 wt % to 90 wt % of hexane, 0 wt % to 90 wt % of hexene, 0 wt % to 50 wt % of methanol, 0 wt % to 50 wt % of ethanol, and 0 wt % to 50 wt % of water, and a total content of methanol, ethanol, and water is greater than or equal to 10 wt %; and
    the riser reactor is configured to feed a catalyst and a riser reactor raw material, and the riser reactor raw material, based on a weight percentage of 100%, comprises 0 wt % to 20 wt % of hydrogen, 0 wt % to 50 wt % of methane, 0 wt % to 50 wt % of ethane, 0 wt % to 20 wt % of ethylene, 0 wt % to 50 wt % of propane, 0 wt % to 20 wt % of propylene, 0 wt % to 90 wt % of butane, 0 wt % to 90 wt % of butene, 0 wt % to 90 wt % of pentane, 0 wt % to 90 wt % of pentene, 0 wt % to 90 wt % of hexane, 0 wt % to 90 wt % of hexene, 0 wt % to 50 wt % of methanol, 0 wt % to 50 wt % of ethanol, and 0 wt % to 50 wt % of water, and a total content of methanol, ethanol, and water is greater than or equal to 10 wt %.

* * * * *